United States Patent
Nakada et al.

(10) Patent No.: US 7,313,435 B2
(45) Date of Patent: Dec. 25, 2007

(54) BIOELECTRIC IMPEDANCE MEASURING APPARATUS

(75) Inventors: Masato Nakada, Shaumburg, IL (US); Koji Oguma, Fujisawa (JP)

(73) Assignee: Tanita Corporation, Tokyo (JP)

( * ) Notice: Subject to any disclaimer, the term of this patent is extended or adjusted under 35 U.S.C. 154(b) by 226 days.

(21) Appl. No.: 10/916,476

(22) Filed: Aug. 12, 2004

(65) Prior Publication Data
US 2005/0054944 A1    Mar. 10, 2005

(30) Foreign Application Priority Data
Sep. 5, 2003    (JP) .............. 2003-313381

(51) Int. Cl.
*A61B 5/05* (2006.01)
(52) U.S. Cl. .................................... 600/547
(58) Field of Classification Search ............... 600/547, 600/32, 35, 509
See application file for complete search history.

(56) References Cited

U.S. PATENT DOCUMENTS

| | | | |
|---|---|---|---|
| 5,335,667 A | | 8/1994 | Cha et al. |
| 5,469,859 A | * | 11/1995 | Tsoglin et al. .............. 600/536 |
| 5,611,351 A | * | 3/1997 | Sato et al. .................. 600/547 |
| 6,007,532 A | * | 12/1999 | Netherly ...................... 606/35 |
| 6,063,075 A | * | 5/2000 | Mihori ......................... 606/35 |
| 6,171,304 B1 | | 1/2001 | Netherly et al. |
| 6,516,222 B2 | * | 2/2003 | Fukuda ...................... 600/547 |
| 7,079,889 B2 | * | 7/2006 | Nakada ...................... 600/547 |
| 2003/0009111 A1 | * | 1/2003 | Cory et al. .................. 600/547 |
| 2003/0040741 A1 | * | 2/2003 | Fleenor et al. ............... 606/32 |
| 2003/0220581 A1 | * | 11/2003 | Ollmar et al. ............... 600/547 |
| 2004/0002662 A1 | * | 1/2004 | Hjelt et al. .................. 600/547 |
| 2004/0167423 A1 | * | 8/2004 | Pillon et al. ................ 600/547 |

FOREIGN PATENT DOCUMENTS

| | | |
|---|---|---|
| JP | 2835656 | 10/1994 |
| JP | 8-154910 | 6/1996 |
| JP | 10-174680 | 6/1998 |
| JP | 2003-52658 | 2/2003 |
| JP | 2003-180647 | 7/2003 |

\* cited by examiner

*Primary Examiner*—Max F. Hindenburg
*Assistant Examiner*—H. Q. Nguyen
(74) *Attorney, Agent, or Firm*—McDermott Will & Emery LLP

(57) ABSTRACT

There is provided an apparatus capable of carrying out an accurate bioelectrical impedance measurement by determining whether contact of a living body with electrodes used at the time of the bioelectrical impedance measurement is normal or not more accurately. The apparatus uses a parameter associated with a phase difference in determining the contact condition of the living body with the electrodes. As the parameter associated with a phase difference, the apparatus uses a value represented by X/R wherein R is a resistance component in a bioelectrical impedance to be measured and X is a reactance component in the bioelectrical impedance and determines that contact of the living body with the electrodes is not normal when the value of X/R is out of a determination range such as a<X/R<b (a and b are real numbers).

9 Claims, 8 Drawing Sheets

BIOELECTRIC IMPEDANCE MEASURING APPARATUS

BACKGROUND OF THE INVENTION (i) Field of the Invention

The present invention relates to a technique for determining the contact condition of electrodes in an apparatus which calculates the composition of a body by measuring a bioelectrical impedance.

(ii) Description of the Related Art

There is an apparatus which calculates fat in a body by measuring a bioelectrical impedance. As a measurement method therefor, a measurement method called a four terminal method is primarily used.

To be more specific about the four terminal method for measuring a bioelectrical impedance, the method measures an impedance in a body between parts, e.g., between both hands or both feet of a subject, and statistically estimates a body fat amount, a muscle amount, a body water amount and the like from the measurement value.

A scale-incorporating body fat meter which measures a body fat percentage as well as a body weight is known. To measure a bioelectrical impedance between both feet with the meter, a subject stands on the meter with the bottoms of both feet in contact with electrodes for feet which are provided on the top surface of the meter, and the bioelectrical impedance is then measured.

In such a measurement method, when satisfactory contact is secured between electrodes and the surface of the skin, measurement can be made without any problems, while when the contact condition of the skin surface with the electrodes is unsatisfactory, a high contact impedance occurs between the skin surface and the electrodes, and an accurate measurement may not be carried out.

As solutions for the problem, a number of methods for checking the contact condition of a subject with electrodes are proposed.

In one method, resistances Ra and Rb having values which are small enough not to influence measurement accuracy are connected to between current applying electrodes A1 and A2 and voltage measuring electrodes B1 and B2, and when a contact impedance is high, a measurement voltage which occurs in an impedance in a body can be determined by applying a high clamp voltage from a constant current circuit to a voltage measuring circuit input, thereby preventing mismeasurement. That is, the contact condition is determined by checking whether the contact impedance is a proper value (for example, Patent Document 1).

Further, there is also a method which determines whether a measurement condition is proper by determining the size of a contact impedance (for example, Patent Document 2).

Further, there is proposed a technique comprising installing a measurement start switch in electrodes to be in contact with a living body at the time of measurement so as to make it easy to obtain a satisfactory contact condition. It is described that a proper measurement posture and a proper contact condition can be obtained thereby (for example, Patent Document 3).

Further, there is proposed a method which uses current supplying electrodes as all electrodes used for measuring a bioelectrical impedance and passing a constant current I while switching connections to the electrodes so as to obtain only in-body impedance values including contact resistances and in-body impedances including contact resistance values (for example, Patent Document 4).

In addition, there is also disclosed an impedance measurement method which comprises serially connecting a plurality of reference resistances of known resistance values which can separate a bioelectrical impedance value to be measured appropriately to a living body in the route of a bioelectrical impedance measuring current, measuring voltage drop values by the resistance values of the reference resistances and a voltage drop value by the living body, determining a correlation equation between the resistance values and corresponding measured voltage values, and determining a bioelectrical impedance value by use of the measured voltage value of the living body and the correlation equation (for example, Patent Document 5).

Patent Document 1
  Japanese Patent Laid-Open No. 8-154910

Patent Document 2
  Japanese Patent Laid-Open No. 2003-52658

Patent Document 3
  Japanese Patent Laid-Open No. 10-174680

Patent Document 4
  Japanese Patent Laid-Open No. 2003-180647

Patent Document 5
  Japanese Patent No. 2,835,656

For a secure measurement of a bioelectrical impedance, good contact must be established between a living body and electrodes. For this reason, as described in Description of the Related Art, methods for checking the contact condition of electrodes in measurement of a bioelectrical impedance have heretofore been proposed. These methods perform checking in addition to measurement of a bioelectrical impedance of a body part to be measured. That is, to measure a bioelectrical impedance between both feet, contact impedances between the bottoms of the feet and the electrodes are measured, and when the results are good, the contact condition of the electrodes is determined to be normal, and a bioelectrical impedance between both feet is measured. Thus, several determination processes must be performed before the measurement, resulting in a long measurement time.

Therefore, in a generally, actually used method for determining the contact condition of electrodes, whether the contact condition is satisfactory or a short may be occurring is determined by determining whether the absolute value of a measured bioelectrical impedance falls within a certain range of values.

However, there have been cases where the contact condition is misjudged as a measurable condition even when satisfactory contact is not established and measurement is actually carried out.

FIG. 9 is a block diagram of a bioelectrical impedance measuring section.

$Z_R$ represents a reference impedance corresponding to a plurality of reference resistances of known resistance values in the impedance measurement method (refer to Japanese Patent No. 2,835,656) described in Description of the Related Art, $Z_B$ represents a bioelectrical impedance to be measured, a and b represent a current supplying electrode, c and d represent a voltage measuring electrode, and ic represents a measurement current.

In general, the measurement current ic passes the reference impedance $Z_R$ and the bioelectrical impedance $Z_B$ without any problems, and complex voltages $V_R$ and $V_B$ thereof are measurable.

When a living body is not in normal contact with either or both of the current supplying electrodes a and b, the measurement circuit becomes an open state, and both $V_R$ and $V_B$ become 0, i.e., unmeasurable. At that time, a very low voltage corresponding to the common mode rejection ratio (CMRR) of an amplifier is obtained as a measurement result and is ideally 0.

Further, when either or both of the voltage measuring electrodes c and d are not in normal contact with the living body, $V_R$ can be measured, but $V_B$ becomes unmeasurable and the value thereof is not settled.

As checking in such a case, the contact condition of the electrodes is determined by setting a proper impedance range such as 200 Ω<|Z|<1000 Ω. However, in some cases, it has become stable at a value which is slightly over 200 Ω.

It is assumed that this has occurred because the voltage of a terminal with improper contact has actually occurred due to the protection circuit (e.g., diode to deal with static electricity) of the amplifier or stray capacitance (e.g., interelectrode capacitance). For example, when the voltage measuring electrode c is open (i.e., when it is not normally contacted) as shown in FIG. 9B, it is assumed that interelectrode capacitance occurs between the voltage measuring electrodes c and d and a voltage which is not supposed to be measured occurs. Thus, even when the contact condition is not normal, the conventional contact determination method using a proper impedance range misjudges that the contact condition is normal because the impedance value falls within the normal range, and continues the measurement and displays an erroneous measurement result.

The present invention has been conceived in view of such a problem. An object of the present invention is to provide an apparatus capable of carrying out an accurate bioelectrical impedance measurement by determining whether contact of a living body with electrodes used at the time of the bioelectrical impedance measurement is normal or not more accurately.

SUMMARY OF THE INVENTION

The present invention is a bioelectrical impedance measuring apparatus comprising an impedance measurement unit for measuring a bioelectrical impedance which comprises electrodes to contact with a living body, and a determination unit for determining the contact condition of a living body with the electrodes by use of a parameter associated with the phase difference of the living body.

Further, in the bioelectrical impedance measuring apparatus of the present invention, when the resistance component in a bioelectrical impedance to be measured in the impedance measurement unit is represented by R and the reactance component in the bioelectrical impedance is represented by X, the parameter associated with the phase difference of the living body is a value represented by X/R.

Further, in the bioelectrical impedance measuring apparatus of the present invention, the condition for determination of the contact in the determination unit is a<X/R<b (a and b are real numbers).

Further, in the bioelectrical impedance measuring apparatus of the present invention, prior to determination of the contact condition of the living body with the electrodes by use of the parameter associated with the phase difference, the determination unit determines the contact condition by determining whether a parameter associated with the resistance component of the bioelectrical impedance to be measured in the impedance measurement unit is a positive value.

Further, in the bioelectrical impedance measuring apparatus of the present invention, the parameter associated with the resistance component is a true impedance component variable representing the resistance component of a true impedance.

Further, in the bioelectrical impedance measuring apparatus of the present invention, the parameter associated with the resistance component is a voltage variable based on the resistance component.

The bioelectrical impedance measuring apparatus of the present invention uses a parameter associated with the phase difference of a living body in determination of the contact condition of the living body with electrodes used at the time of measuring a bioelectrical impedance. Thus, the contact condition can be determined more accurately than before. Thereby, an accurate bioelectrical impedance value can be measured, and the values of body compositions such as a body fat percentage and a muscle amount which are computed by use of the bioelectrical impedance value also become accurate.

Further, in the bioelectrical impedance measuring apparatus of the present invention, a value represented by X/R wherein R represents the resistance component in a bioelectrical impedance to be measured and X represents the reactance component of the bioelectrical impedance is used in determination of the contact condition of a living body with the electrodes used at the time of measuring the bioelectrical impedance. This value shows a significantly different value from the corresponding value of the living body when contact of the electrodes is not normal. Thereby, the contact condition can be determined easily and accurately.

Further, in the bioelectrical impedance measuring apparatus of the present invention, a condition: a<X/R<b (a and b are real numbers) is set, the contact condition is determined by checking whether a calculated value is within the range, and when the calculated value is out of the range, it is determined that the contact condition is not normal. Thus, determination of the contact condition can be made easily.

Further, in the bioelectrical impedance measuring apparatus of the present invention, prior to determination of the contact condition of the living body with the electrodes by use of the parameter associated with the phase difference, it is determined whether a parameter associated with the resistance component of a bioelectrical impedance to be measured is a positive value. Thus, the abnormality of the contact can be checked without performing computation for checking the contact of the living body with the electrodes by use of the parameter associated with the phase difference.

Further, in the bioelectrical impedance measuring apparatus of the present invention, a true impedance component variable $R_B$ representing the resistance component of a true impedance is used as the parameter associated with the resistance component of a bioelectrical impedance to be measured. Thus, without performing the computation for checking the contact of the living body with the electrodes by use of the parameter associated with the phase difference, the contact condition can be determined at the point when the true impedance component variable $R_B$ is computed, and when the contact condition is determined to be not normal, the result of determination using the parameter associated with the phase difference can be known at this point, resulting in a significant reduction in a time required for determination of the contact condition.

Further, in the bioelectrical impedance measuring apparatus of the present invention, a measured voltage variable $V_{BR}$ representing a voltage based on the resistance component is used as the parameter associated with the resistance component of a bioelectrical impedance to be measured. Thus, without performing the computation for checking the contact of the living body with the electrodes by use of the parameter associated with the phase difference, the contact condition can be determined from the value of a voltage measured in the living body, and when the contact condition is determined to be not normal, the result of determination using the parameter associated with the phase difference can be known at this point, resulting in a significant reduction in a time required for determination of the contact condition.

DETAILED DESCRIPTION OF THE PREFERRED EMBODIMENTS

The bioelectrical impedance measuring apparatus of the present invention uses a parameter associated with a phase difference for determination of the contact condition of a living body with electrodes used at the time of measuring a bioelectrical impedance, thereby determining the contact condition more accurately than conventionally used determination methods.

As the parameter associated with a phase difference, a value represented by X/R wherein R represents the resistance component in a bioelectrical impedance to be measured and X represents the reactance component of the bioelectrical impedance is used, and a determination condition such as a<X/R<b (a and b are real numbers) is set. When it is out of this range, it is determined that contact of the living body with the electrodes is not normal.

Further, in addition to determination of the contact condition by use of the parameter associated with the phase difference, it is also determined whether a parameter associated with the resistance component of a bioelectrical impedance to be measured is a positive value. When the value is determined to be a negative value by this checking, the contact condition is determined to be not normal in the subsequent determination of the contact condition by use of the parameter associated with the phase difference. Therefore, the contact condition can still be determined only by the determination of whether the parameter associated with the resistance component of the bioelectrical impedance is a positive value or negative value. The parameter associated with the resistance component of the bioelectrical impedance may be a true impedance component variable $R_B$ representing the resistance component of a true impedance or a measured voltage variable $V_{BR}$ representing a voltage based on the resistance component.

EXAMPLE 1

An example of the present invention will be described by use of the drawings.

Figure 1:
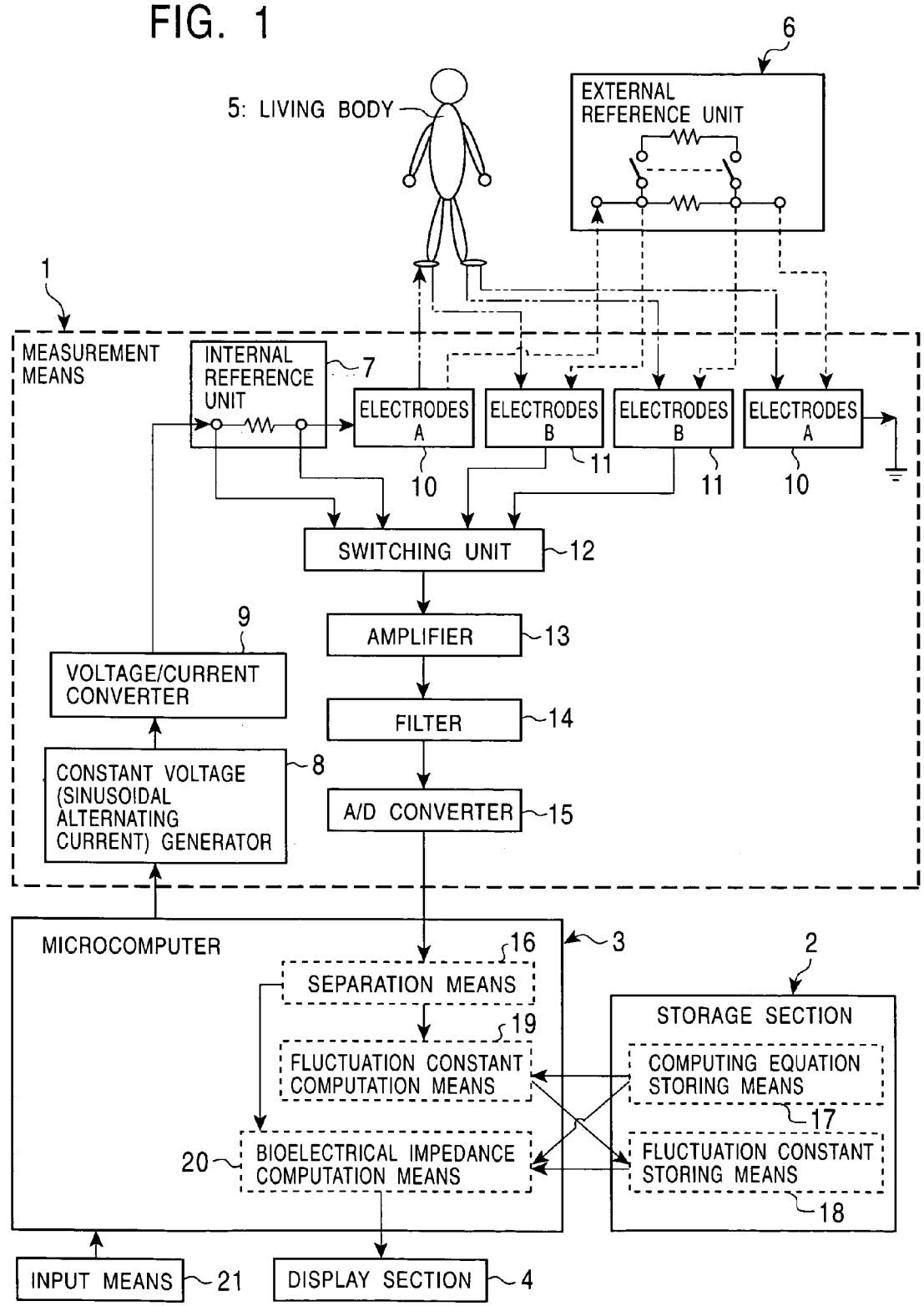
FIG. 1 is a block diagram illustrating the configuration of a body fat meter of the present invention.

FIG. 1 is a block diagram of a body fat meter using the bioelectrical impedance measuring apparatus of the present invention.

The bioelectrical impedance measuring apparatus in the body fat meter separates a measured impedance of a living body into a resistance component and a reactance component by software-like processing so as to determine a more accurate impedance of the living body.

The body fat meter comprises measuring means 1, a storage section 2, a microcomputer 3, and a display section 4.

In the measurement means 1, a voltage based on the impedance of a living body 5, external reference unit 6 or internal reference unit 7 is measured. The measurement means 1 comprises a constant voltage (sinusoidal alternating current) generator 8, a voltage/current converter 9, the internal reference unit 7, electrodes A10, electrodes B11, a switching unit 12, an amplifier 13, a filter 14, and an A/D converter (synchronous detection type) 15.

The constant voltage (sinusoidal alternating current) generator 8 generates a constant voltage of high frequency (e.g., 50 kHz) and outputs it to the voltage/current converter 9. The voltage/current converter 9 converts the constant voltage output from the constant voltage (sinusoidal alternating current) generator 8 into a constant current and outputs the current to the internal reference unit 7.

The internal reference unit 7 is an impedance serving as a reference for correcting the influence, on an impedance, of a change in the constant current from the constant voltage (sinusoidal alternating current) generator 8 or voltage/current converter 9 that is caused by a change in the temperature of the environment or the like. The internal reference unit 7 corresponds to a group of known reference resistance values in the impedance measurement method (refer to Japanese Patent No. 2,835,656) cited in Description of the Related Art. In the present invention, one known reference resistance is used as the internal reference unit 7.

The electrodes A10 are terminals for detecting a voltage generated in the living body 5 or external reference unit 6 by a constant current output from the voltage/current converter 9 and having passed through the internal reference unit 7.

The switching unit 12 switches between detection of a voltage generated in the internal reference unit 7 by passage of a constant current through the internal reference unit 7 and detection of a voltage generated between the two electrodes B11 by passage of a constant current through the living body 5 or external reference unit 6 between the two electrodes B11.

The amplifier 13 amplifies a voltage having passed through the switching unit 12, i.e., a voltage based on the impedance of the internal reference unit 7 or a voltage based on the impedance of the living body 5 or external reference unit 6. The filter 14 removes noise from a voltage amplified by the amplifier 13.

The A/D converter (synchronous detection type) 15 not only digitizes a voltage (analog) from which noise has been removed by the filter 14 but also separates the voltage into a voltage based on the resistance component and a voltage based on the reactance component of the internal reference unit 7 or the living body 5 or external reference unit 6 based on timing signals corresponding to generation of a sinusoidal wave from the constant voltage (sinusoidal alternating current) generator 8 and outputs the voltages to the microcomputer 3.

The storage section 2 has computing equation storing means 17 and fluctuation constant storing means 18 and is responsible for temporary data storage during various calculations and other known data storages. EEPROM is used in the storage section 2.

The computing equation storing means 17 stores in advance an impedance computing equation which relates true impedance variables representing the resistance component and reactance component of the true impedance of the living body 5 or external reference unit 6 to fluctuation constants representing fluctuations based on impedance fluctuation factors occurring in the measurement means 1 and measured voltage variables representing a voltage based on the resistance component of an impedance by actual measurement and a voltage based on the reactance component of the impedance.

The impedance computing equation is an equation 1 to be described later based on a circuit model in the measurement means 1 in FIG. 2 which takes into consideration fluctuations based on impedance fluctuation factors occurring in the measurement means 1.

Figure 2:
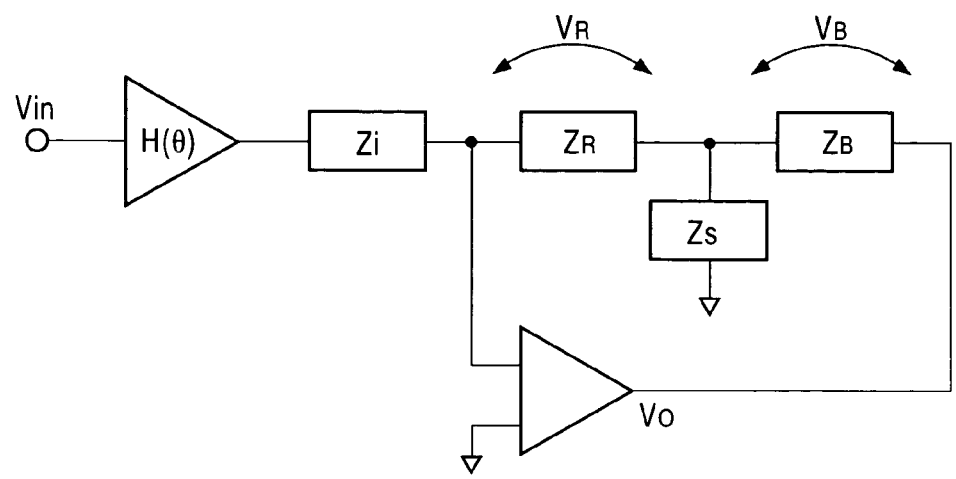
FIG. 2 is a circuit model in measurement means.

In FIG. 2, H(θ) represents a phase fluctuation component occurring in the measurement means 1, $Z_i$ represents the impedance of the voltage/current converter 9, $Z_R$ represents the impedance of the internal reference unit 7, $Z_S$ represents an impedance by stray capacitance or the like, $Z_B$ represents the impedance of the living body 5 or external reference unit 6, $V_o$ represents a voltage occurring from the internal reference unit 7 to the living body 5 (or external reference unit 6), $V_R$ represents a voltage occurring by the impedance component of the internal reference unit 7, and $V_B$ represents a voltage occurring by the impedance component of the living body 5 or external reference unit 6.

According to this circuit model, the impedance of the living body 5 or external reference unit 6 is represented by the equation: $Z_B = V_B(1-Z_R/Z_S)Z_R/V_R = CV_B/V_R$ wherein C represents a fluctuation variable representing fluctuations based on a scale factor and a phase. Then, the equation 1 is derived from taking into consideration a fluctuation variable $V_{OS}$ representing fluctuations based on an offset voltage attributable primarily to $Z_S$ and separating the variables in the above equation and $V_{OS}$ into resistance components and reactance components (i.e., separating $Z_B$ into a true impedance component variable $R_B$ representing the resistance component of the true impedance of the living body 5 or external reference unit 6 and a true impedance component variable $X_B$ representing the reactance component of the true impedance of the living body 5 or external reference unit 6, separating C into a fluctuation variable $C_R$ representing fluctuations based on the scale factor and phase of the resistance component and a fluctuation variable $C_X$ representing fluctuations based on the scale factor and phase of the reactance component, separating $V_B$ into a measured voltage variable $V_{BR}$ representing a voltage based on the resistance component of the living body 5 or external reference unit 6 and a measured voltage variable $V_{BX}$ representing a voltage based on the reactance component of the living body 5 or external reference unit 6, separating $V_R$ into a measured voltage variable $V_{RR}$ representing a voltage based on the resistance component of the internal reference unit 7 and a measured voltage variable $V_{RX}$ representing a voltage based on the reactance component of the internal reference unit 7, and separating $V_{OS}$ into a fluctuation variable $V_{OSR}$ representing fluctuations based on an offset voltage in the resistance component axis direction and a fluctuation variable $V_{OSX}$ representing fluctuations based on an offset voltage in the reactance component axis direction).

$$\begin{pmatrix} R_B \\ X_B \end{pmatrix} = \begin{pmatrix} C_R \\ C_X \end{pmatrix} \times \frac{\begin{pmatrix} V_{BR} \\ V_{BX} \end{pmatrix}}{\begin{pmatrix} V_{RR} \\ V_{RX} \end{pmatrix}} + \begin{pmatrix} V_{OSR} \\ V_{OSX} \end{pmatrix}$$

The fluctuation variables $C_R$ and $C_X$ representing fluctuations based on the scale factors and phases and the fluctuation variables $V_{OSR}$ and $V_{OSX}$ representing fluctuations based on the offset voltages in the equation 1 correspond to fluctuation variables representing fluctuations based on impedance fluctuation factors occurring in the measurement means 1.

Figure 3:
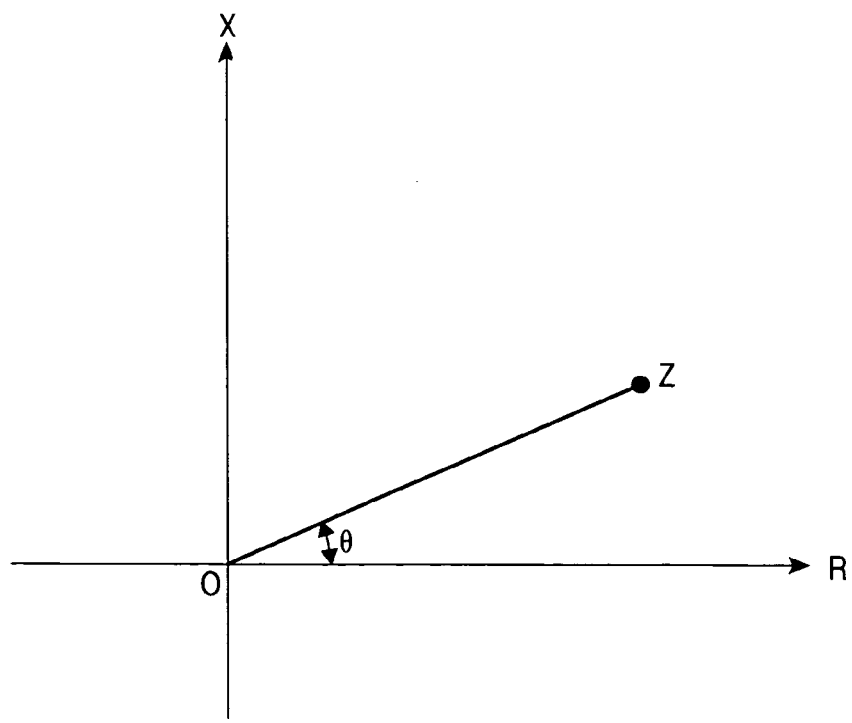
FIG. 3 is a coordinate diagram illustrating the relationship between the resistance component and reactance component of an impedance.

FIG. 3 is a diagram showing the relationship between the resistance component and reactance component of an impedance in the coordinate system. The vertical axis X represents a reactance component, the horizontal axis R represents a resistance component, the point Z represents an impedance, the coordinate intersection O represents the zero point, and the deflection angle θ represents a phase difference. The fluctuation variables $C_R$ and $C_X$ representing fluctuations based on the scale factors and phases represent variables for fluctuations in the direction of the line segment OZ and fluctuations of the deflection angle θ, and the fluctuation variables $V_{OSR}$ and $V_{OSX}$ representing fluctuations based on the offset voltages represent variables for fluctuations of the coordinate intersection O.

The fluctuation constant storing means 18 stores a fluctuation constant computed by fluctuation constant computation means 19 to be described later.

The microcomputer 3 comprises separation means 16, the fluctuation constant computation means 19 and bioelectrical impedance computation means 20 and performs control of generation of a high-frequency constant voltage from the constant voltage (sinusoidal alternating current) generator 8 and other known controls. Further, although not shown in the drawing, the microcomputer 3 also has common functions in microcomputers, such as RAM for storing data temporarily and a timer function for counting a given time.

The separation means 16 computes a voltage based on the resistance component and a voltage based on the reactance component by actual measurement of the internal reference unit 7 or the living body 5 or external reference unit 6, based on the voltages based on the impedance which have been output from the A/D converter 15 and an amplitude resulting from time-dividing the same period as that of a sinusoidal wave generated from the constant voltage (sinusoidal alternating current) generator 8 or a period 90° ahead of the period of the sinusoidal wave.

The fluctuation constant computation means 19 computes a fluctuation constant which is a constant of the fluctuation variable from the impedance computing equation (equation 1) stored in advance in the computing equation storing means 17, based on the voltage based on the resistance component and the voltage based on the reactance component which have been separated by the computation in the separation means 16 by measurements of the internal reference unit 7 and the external reference unit 6 and the known resistance component and reactance component of the impedance of the external reference unit 6 measured in the measurement means 1.

The bioelectrical impedance computation means 20 substitutes the fluctuation constant stored in the fluctuation constant storing means 18 and the voltage based on the resistance component and the voltage based on the reactance component of the impedance of the living body 5 which are measured in the measurement means 1 and separated in the separation means 16 into the impedance computing equation (equation 1) stored in advance in the computing equation storing means 17 so as to compute the resistance component and reactance component of the true impedance of the living body 5.

The display section 4 displays the results of the computations preformed in the bioelectrical impedance computation means 20.

Input means 21 allows key entry of data to the body fat meter and comprises a plurality of switches such as a setting switch, a measurement switch and numerical switches.

Figure 4:
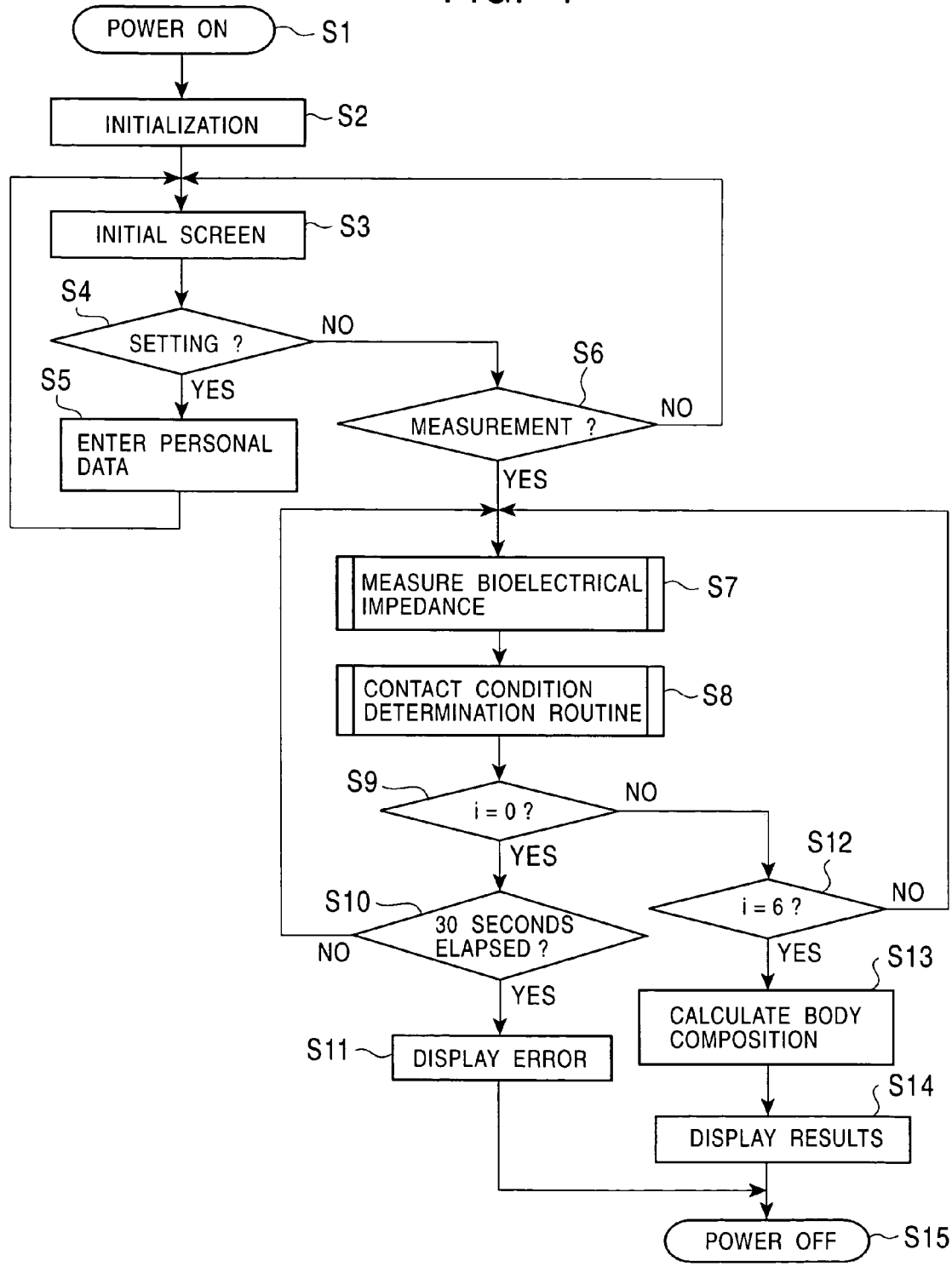
FIG. 4 is a main flowchart illustrating the flow of operations of the body fat meter of the present invention.

Next, the flow of use and operation of the body fat meter according to the present example will be described with reference to the flowchart shown in FIG. 4.

When the power of the body fat meter is turned on (STEP S1), the microcomputer 3 connects the units and initializes values in RAM (STEP S2).

Then, a message urging a subject to enter his/her sex, height and body weight is displayed on the display section 4 (STEP S3). At the press of the setting switch of the input means 21 (STEP S4), the body fat meter enters a personal data entry mode, and the subject enters personal data such as sex, a body height and a body weight by use of the numerical switches (STEP S5).

If the measurement switch is pressed in place of the setting switch in STEP S4 (STEP S6), the body fat meter enters a bioelectrical impedance measuring mode and a timer in the microcomputer starts (STEP S7). This bioelectrical impedance measuring routine will be described later.

After a bioelectrical impedance is measured, a contact condition determination routine which determines from the measured value if the living body is in proper contact with the electrodes is executed (STEP S8). This contact condition determination routine will be described later.

In the contact condition determination routine, the value of the number i of normal contacts is checked to check whether the contact condition is normal (STEP S9). If the contact condition is not normal, the microcomputer 3 checks from the timer installed therein whether 30 seconds have elapsed from the start of the bioelectrical impedance measuring mode (STEP S10). If 30 seconds have not yet elapsed, the microcomputer 3 returns to the bioelectrical impedance measuring routine in STEP S7 and continues the measurement, while if 30 seconds have already elapsed, the microcomputer 3 determines that an accurate measurement could not be made this time and displays an error on the display section 4 (STEP S11).

If the contact condition is normal in STEP S9, the microcomputer 3 checks whether the contact condition has been determined to be normal 6 times in a row. The microcomputer 3 checks whether the value of i which represents the number of normal contacts and is stored in the RAM installed in the microcomputer 3 is 6 (STEP S12). If the value of i is less than 6, the microcomputer 3 returns to STEP S7 and continues measurement of the bioelectrical impedance. Meanwhile, if the value of i is more than 6, the microcomputer 3 determines that the contact condition is absolutely normal, calculates a body fat percentage (STEP S13) and displays the result of the calculation on the display section 4 (STEP S14).

Upon passage of a give time after display of the error in STEP S11 and display of the measurement result in STEP S14, the display is shut down, and the power of the body fat meter is also turned off automatically (STEP S15).

Next, the bioelectrical impedance measuring routine in STEP S7 will be described. Firstly, as shown in FIG. 1, the external reference unit 6 which is a known impedance (e.g., $R=100\ \Omega$, $X=0\ \Omega$) corresponding to the lower limit of the measurement range of bioelectrical impedance is connected to the electrodes A10 and the electrodes B11 (STEP S21).

Then, under control of the microcomputer 3, a constant voltage of high frequency (e.g., 50 kHz) is generated in the constant voltage (sinusoidal alternating current) generator 8 and converted into a constant current in the voltage/current converter 9, and the constant current is output to the internal reference unit 7. Then, the switching unit 12 is connected to the internal reference unit 7 which is a known impedance (e.g., $R=800\ \Omega$, $X=0\ \Omega$), a voltage which occurs in the internal reference unit 7 is detected, the voltage is amplified by the amplifier 13, noise is removed from the amplified voltage by the filter 14, and the resulting voltage (analog) is converted into a digital signal by the A/D converter 15 and then output to the separation means 16 in the microcomputer 3.

Figure 5:
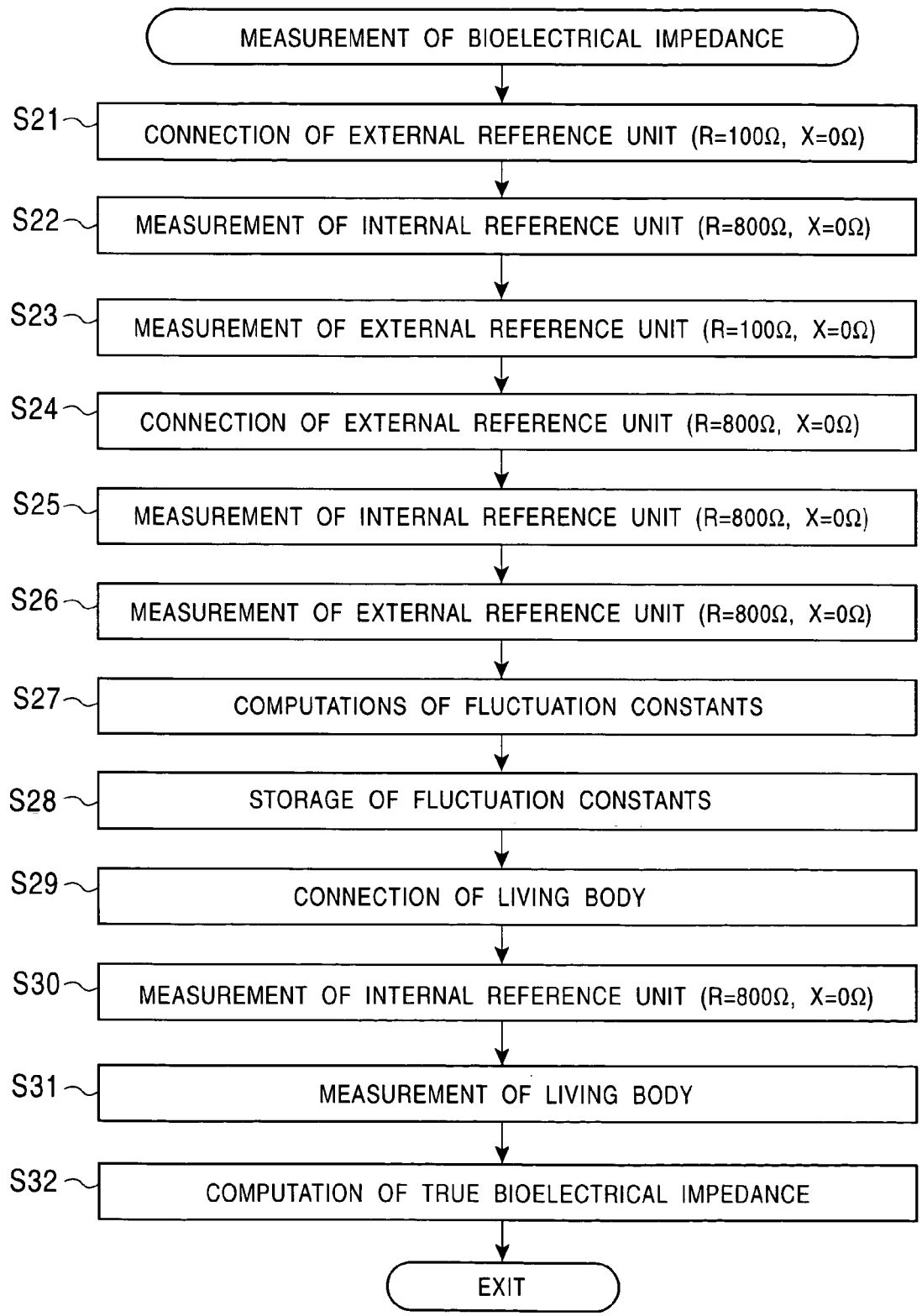
FIG. 5 is a flowchart illustrating a bioelectrical impedance measuring subroutine in the flowchart of FIG. 4.

Then, in the separation means 16 in the microcomputer 3, processes shown in the flowchart of FIG. 5 are performed so as to compute a voltage based on the resistance component of the impedance by actual measurement of the internal reference unit 7 and a voltage based on the reactance component thereof (STEP S22).

The processes in STEP S22 will be described more specifically by use of FIG. 6. After cumulative buffers for an R component voltage and an X component voltage in the separation means 16 are cleared (STEP S41), a cumulative counter in the separation means 16 is set at n=0 (STEP S42) and an interrupt occurring mode is activated (STEP S43), the A/D converter 15 is executed (STEP S44), and the separation means 16 takes in a voltage (V(t)) based on an impedance which is a digital signal output from the A/D converter 15 (STEP S45). Then, the separation means 16 reads in an amplitude ($\sin\theta_1$) resulting from time-dividing the same period as that of a sinusoidal wave generated from the constant voltage (sinusoidal alternating current) generator 8, from the ROM table in the microcomputer 3 (STEP S46). Then, the separation means 16 multiplies the voltage (V(t)) based on the impedance by actual measurement of the internal reference unit 7 by the amplitude ($\sin\theta_1$) resulting from time-dividing the same period as that of a sinusoidal wave generated from the constant voltage (sinusoidal alternating current) generator 8 which has been read in from the ROM table in the microcomputer 3 (STEP S47) and adds the resulting product to the R component voltage cumulative buffer (STEP S48). Then, the separation means 16 reads in an amplitude ($\cos\theta_1$) resulting from time-dividing a period which is 90° ahead of the period of a sinusoidal wave generated from the constant voltage (sinusoidal alternating current) generator 8, from the ROM table in the microcomputer 3 (STEP S49). Then, the separation means 16 multiplies the voltage (V(t)) based on the impedance by actual measurement of the internal reference unit 7 by the amplitude ($\cos\theta_1$) resulting from time-dividing a period which is 90° ahead of the period of a sinusoidal wave generated from the constant voltage (sinusoidal alternating current) generator 8 which has been read in from the ROM table in the microcomputer 3 (STEP S50) and adds the resulting product to the X component voltage cumulative buffer (STEP S51). Then, when the cumulative counter satisfies n<32 ("YES" in STEP S52), the separation means 16 increments the cumulative counter by 1 (STEP S53) and returns to STEP S43 and repeats the processes. In STEP S46 and STEP S49 in that case, time-divided amplitudes sin $\theta_1$ and cos $\theta_1$ whose i has been incremented sequentially are read in. Meanwhile, when the cumulative counter fails to satisfy n<32 ("NO" in STEP S52), the separation means 16 stores measured voltage variables $V_{RR}$ and $V_{RX}$ accumulated in the R component voltage cumulative buffer and the X component voltage cumulative buffer in the storage section 2 temporarily (STEP S54).

Then, the switching unit 12 is connected to the external reference unit 6 (R=100 Ω, X=0 Ω) in place of the internal reference unit 7, a voltage which occurs in the external reference unit 6 is detected, the voltage is amplified by the amplifier 13, noise is removed from the amplified voltage by the filter 14, and the resulting voltage (analog) is converted into a digital signal by the A/D converter 15 and then output to the separation means 16 in the microcomputer 3.

Figure 6:
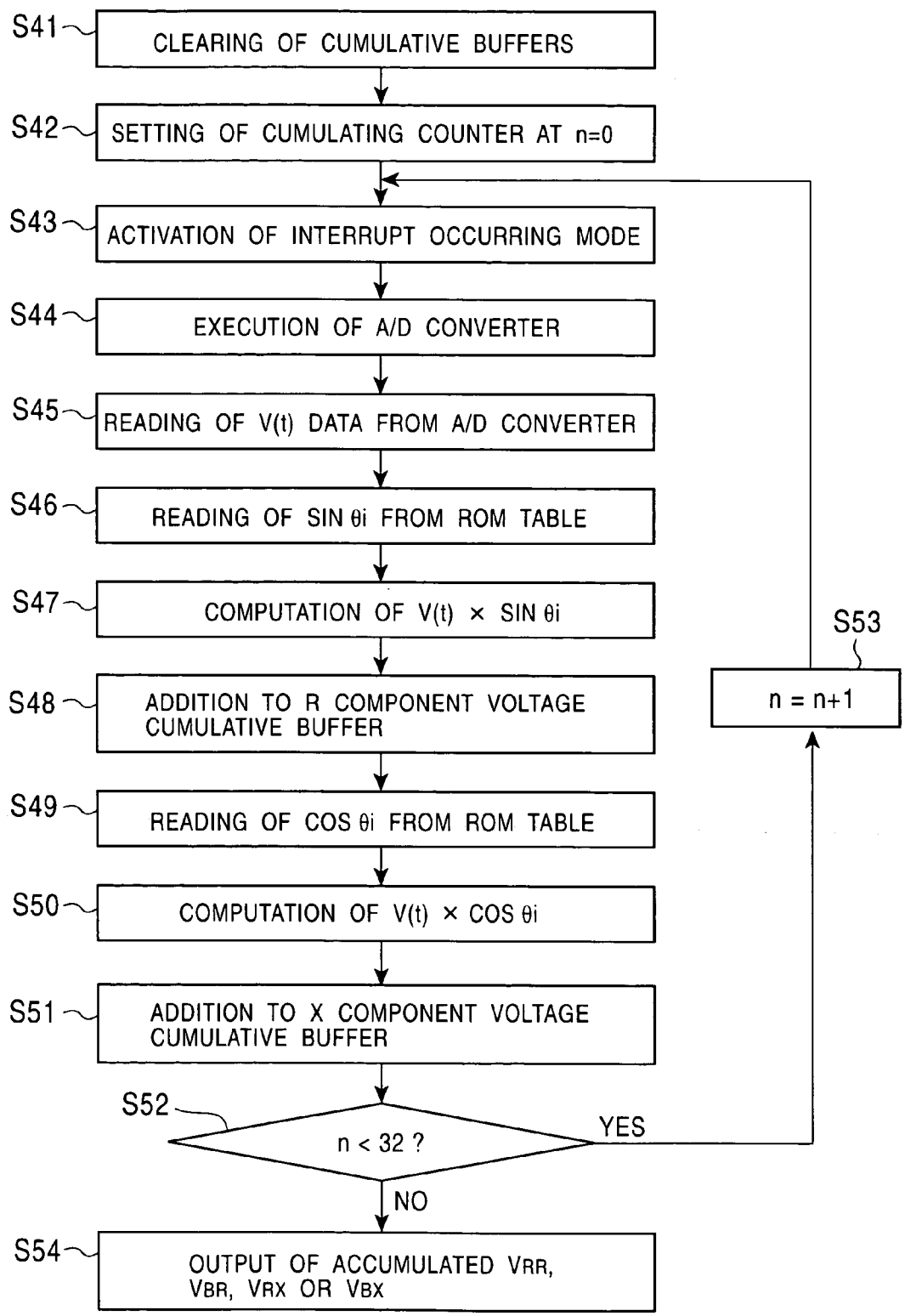
FIG. 6 is a flowchart illustrating the flow of processes in separation means 16 in the flowchart of FIG. 5.

Then, in the separation means 16 in the microcomputer 3, the processes shown in the flowchart of FIG. 6 are performed so as to compute a voltage based on the resistance component of the impedance by actual measurement of the external reference unit 6 and a voltage based on the reactance component thereof (STEP S23).

The processes in STEP S23 will be described more specifically by use of FIG. 6. After cumulative buffers for an R component voltage and an X component voltage in the separation means 16 are cleared (STEP S41), a cumulative counter in the separation means 16 is set at n=0 (STEP S42) and an interrupt occurring mode is activated (STEP S43), the A/D converter 15 is executed (STEP S44), and the separation means 16 takes in a voltage (V(t)) based on an impedance which is a digital signal output from the A/D converter 15 (STEP S45). Then, the separation means 16 reads in an amplitude (sin $\theta_1$) resulting from time-dividing the same period as that of a sinusoidal wave generated from the constant voltage (sinusoidal alternating current) generator 8, from the ROM table in the microcomputer 3 (STEP S46). Then, the separation means 16 multiplies the voltage (V(t)) based on the impedance by actual measurement of the external reference unit 6 by the amplitude (sin $\theta_1$) resulting from time-dividing the same period as that of a sinusoidal wave generated from the constant voltage (sinusoidal alternating current) generator 8 which has been read in from the ROM table in the microcomputer 3 (STEP S47) and adds the resulting product to the R component voltage cumulative buffer (STEP S48). Then, the separation means 16 reads in an amplitude (cos $\theta_1$) resulting from time-dividing a period which is 90° ahead of the period of a sinusoidal wave generated from the constant voltage (sinusoidal alternating current) generator 8, from the ROM table in the microcomputer 3 (STEP S49). Then, the separation means 16 multiplies the voltage (V(t)) based on the impedance by actual measurement of the external reference unit 6 by the amplitude (cos $\theta_1$) resulting from time-dividing a period which is 90° ahead of the period of a sinusoidal wave generated from the constant voltage (sinusoidal alternating current) generator 8 which has been read in from the ROM table in the microcomputer 3 (STEP S50) and adds the resulting product to the X component voltage cumulative buffer (STEP S51). Then, when the cumulative counter satisfies n<32 ("YES" in STEP S52), the separation means 16 increments the cumulative counter by 1 (STEP S53) and returns to STEP S43 and repeats the processes. In STEP S46 and STEP S49 in that case, time-divided amplitudes sin $\theta_1$ and cos $\theta_1$ whose i has been incremented sequentially are read in. Meanwhile, when the cumulative counter fails to satisfy n<32 ("NO" in STEP S52), the separation means 16 stores measured voltage variables $V_{BR}$ and $V_{BX}$ accumulated in the R component voltage cumulative buffer and the X component voltage cumulative buffer in the storage section 2 temporarily (STEP S54).

Then, to the electrodes A10 and the electrodes B11, the external reference unit 6 which is a known impedance (e.g., R=800 Ω, X=0 Ω) corresponding to the upper limit of the measurement range of bioelectrical impedance is connected in place of the external reference unit 6 which is a known impedance (e.g., R=100 Ω, X=0 Ω) corresponding to the lower limit of the measurement range of bioelectrical impedance (STEP S24).

Then, processes similar to those in STEP S22 are carried out, and a voltage based on the resistance component of the internal reference unit 7 and a voltage based on the reactance component of the internal reference unit 7 are stored in the storage section 2 temporarily (STEP S25).

Then, processes similar to those in STEP S23 are carried out, and a voltage based on the resistance component of the external reference unit 6 which is a known impedance (e.g., R=800 Ω, X=0 Ω) corresponding to the upper limit of the measurement range of bioelectrical impedance and a voltage based on the reactance component of the external reference unit 6 are stored in the storage section 2 temporarily (STEP S26).

Then, in the fluctuation constant computation means 19, firstly, the voltage based on the resistance component and the voltage based on the reactance component which are stored in the storage section 2 temporarily in STEP S23 and the resistance component and reactance component of the impedance of the external reference unit 6 connected to the electrodes A10 and the electrodes B11 in STEP S21 are substituted into the equation 1 so as to form a first equation. To be more specific, the first equation is formed by substituting a voltage based on the resistance component (R=800 Ω) of the internal reference unit (R=800 Ω, X=0 Ω) 7 at the time of connecting to the external reference unit 6 (R=100 Ω, X=0 Ω) into the measured voltage variable $V_{RR}$ in the equation 1, substituting a voltage based on the reactance component (X=0 Ω) of the internal reference unit (R=800 Ω, X=0 Ω) 7 at the time of connecting to the external reference unit 6 (R=100 Ω, X=0 Ω) into the measured voltage variable $V_{RX}$, substituting a voltage based on the resistance component (R=100 Ω) of the external reference unit 6 (R=100 Ω, X=0 Ω) at the time of connecting to the external reference unit 6 into the measured voltage variable $V_{BR}$, substituting a voltage based on the reactance component (X=0 Ω) of the external reference unit 6 (R=100 Ω, X=0 Ω) at the time of connecting to the external reference unit 6 into the measured voltage variable $V_{BX}$, substituting the resistance component (R=100 Ω) of the external reference unit 6 (R=100 Ω, X=0 Ω) at the time of connecting to the external reference unit 6 into the true impedance component variable $R_B$, and substituting the reactance component (X=0 Ω) of the external reference unit 6 (R=100 Ω, X=0 Ω) at the time of connecting to the external reference unit 6 into the true impedance component variable $X_B$.

Then, the voltage based on the resistance component and the voltage based on the reactance component which are stored in the storage section 2 temporarily in STEP S26 and the resistance component and reactance component of the impedance of the external reference unit 6 connected to the electrodes A10 and the electrodes B11 in STEP S24 are substituted into the equation 1 so as to form a second equation. To be more specific, the second equation is formed by substituting a voltage based on the resistance component (R=800 Ω) of the internal reference unit (R=800 Ω, X=0 Ω) 7 at the time of connecting to the external reference unit 6 (R=800 Ω, X=0 Ω) into the measured voltage variable $V_{RR}$ in the equation 1, substituting a voltage based on the reactance component (X=0 Ω) of the internal reference unit (R=800 Ω, X=0 Ω) 7 at the time of connecting to the external reference unit 6 (R=800 Ω, X=0 Ω) into the measured voltage variable $V_{RX}$, substituting a voltage based on the resistance component (R=800 Ω) of the external reference unit 6 (R=800 Ω, X=0 Ω) at the time of connecting to the external reference unit 6 into the measured voltage variable $V_{BR}$, substituting a voltage based on the reactance component (X=0 Ω) of the external reference unit 6 (R=800 Ω, X=0 Ω) at the time of connecting to the external reference unit 6 into the measured voltage variable $V_{BX}$, substituting the resistance component (R=800 Ω) of the external reference unit 6 (R=800 Ω, X=0 Ω) at the time of connecting to the external reference unit 6 into the true impedance component variable $R_B$, and substituting the reactance component (X=0 Ω) of the external reference unit 6 (R=800 Ω, X=0 Ω) at the time of connecting to the external reference unit 6 into the true impedance component variable $X_B$.

Then, the first equation and the second equation are solved as simultaneous equations so as to determine constants (fluctuation constants) for the fluctuation variables $C_R$ and $C_X$ and constants (fluctuation constants) for the measured voltage variables $V_{OSR}$ and $V_{OSX}$ (STEP S27).

Then, the thus obtained fluctuation constants are stored in the fluctuation constant storing means 18 (STEP S28). The voltages based on the resistance components and the voltages based on the reactance components which have been temporarily stored in the storage section 2 may be erased at this point or later.

Then, as shown in FIG. 1, body parts of the living body 5 are connected to the electrodes A10 and the electrodes B11 (STEP S29).

Then, processes similar to those in STEP S22 are carried out, and a voltage based on the resistance component of the internal reference unit 7 and a voltage based on the reactance component of the internal reference unit 7 are stored in the storage section 2 temporarily (STEP S30).

Then, the switching unit 12 is connected to the living body 5 in place of the internal reference unit 7, a voltage which occurs in the living body 5 is detected, the voltage is amplified by the amplifier 13, noise is removed from the amplified voltage by the filter 14, and the resulting voltage (analog) is converted into a digital signal by the A/D converter 15 and then output to the separation means 16 in the microcomputer 3.

Then, in the separation means 16 in the microcomputer 3, processes as shown in the flowchart of FIG. 6 are performed so as to compute a voltage based on the resistance component by actual measurement of the living body 5 and a voltage based on the reactance component thereof (STEP S31).

The processes in STEP S31 will be described more specifically by use of FIG. 6. After cumulative buffers for an R component voltage and an X component voltage in the separation means 16 are cleared (STEP S41), a cumulative counter in the separation means 16 is set at n=0 (STEP S42) and an interrupt occurring mode is activated (STEP S43), the A/D converter 15 is executed (STEP S44), and the separation means 16 takes in a voltage (V(t)) based on an impedance which is a digital signal output from the A/D converter 15 (STEP S45). Then, the separation means 16 reads in an amplitude (sin $\theta_1$) resulting from time-dividing the same period as that of a sinusoidal wave generated from the constant voltage (sinusoidal alternating current) generator 8, from the ROM table in the microcomputer 3 (STEP S46). Then, the separation means 16 multiplies the voltage (V(t)) based on the impedance by actual measurement of the living body 5 by the amplitude (sin $\theta_1$) resulting from time-dividing the same period as that of a sinusoidal wave generated from the constant voltage (sinusoidal alternating current) generator 8 which has been read in from the ROM table in the microcomputer 3 (STEP S47) and adds the resulting product to the R component voltage cumulative buffer (STEP S48). Then, the separation means 16 reads in an amplitude (cos $\theta_1$) resulting from time-dividing a period which is 90° ahead of the period of a sinusoidal wave generated from the constant voltage (sinusoidal alternating current) generator 8, from the ROM table in the microcomputer 3 (STEP S49). Then, the separation means 16 multiplies the voltage (V(t)) based on the impedance by actual measurement of the living body 5 by the amplitude (cos $\theta_1$) resulting from time-dividing a period which is 90° ahead of the period of a sinusoidal wave generated from the constant voltage (sinusoidal alternating current) generator 8 which has been read in from the ROM table in the microcomputer 3 (STEP S50) and adds the resulting product to the X component voltage cumulative buffer (STEP S51). Then, when the cumulative counter satisfies n<32 ("YES" in STEP S52), the separation means 16 increments the cumulative counter by 1 (STEP S53) and returns to STEP S43 and repeats the processes. In STEP S46 and STEP S49 in that case, time-divided amplitudes sin $\theta_i$ and cos $\theta_i$ whose i has been incremented sequentially are read in. Meanwhile, when the cumulative counter fails to satisfy n<32 ("NO" in STEP S52), the separation means 16 outputs measured voltage variables $V_{BR}$ and $V_{BX}$ accumulated in the R component voltage cumulative buffer and the X component voltage cumulative buffer to the bioelectrical impedance computation means 20 (STEP S54).

Then, in the bioelectrical impedance computation means 20, the output voltage based on the resistance component of the living body 5, the output voltage based on the reactance component of the living body 5, and the fluctuation constants stored in the fluctuation constant storing means 18 are substituted into the equation 1 stored in the computing equation storing means 17 so as to compute the resistance component $R_B$ of the true impedance of the living body 5 and the reactance component $X_B$ of the true impedance of the living body 5. To be more specific, the resistance component $R_B$ of the true impedance of the living body 5 and the reactance component $X_B$ of the true impedance of the living body 5 are computed by substituting the voltage based on the resistance component of the living body 5 which has been separated in the separation means 16 into the measured voltage variable $V_{BR}$ in the equation 1, substituting the voltage based on the reactance component of the living body 5 into the measured voltage variable $V_{BX}$, substituting the voltage based on the resistance component of the internal reference unit 7 which is stored temporarily in the storage section 2 in STEP S31 into the measured voltage variable $V_{RR}$, substituting the voltage based on the reactance component of the internal reference unit 7 into the measured voltage variable $V_{RX}$, substituting the fluctuation constants stored in the fluctuation constant storing means 18 in STEP S28 into the fluctuation variables $C_R$ and $C_X$, and substituting the fluctuation constants for correcting offset voltages into the fluctuation variables $V_{OSR}$ and $V_{OSX}$, followed by output of the resistance component $R_B$ and the reactance component $X_B$ (STEP S32).

Thereby, a series of procedures are completed.

As described above, the bioelectrical impedance measuring apparatus of the present invention measures a voltage based on the impedance of an object to be measured (living body, external reference unit, internal reference unit) by the measurement means and separates the measured voltage into a voltage based on a resistance component and a voltage based on a reactance component by the separation means based on software-like means. Thereby, it can be separated into a resistance component and a reactance component which are closely related to impedance fluctuation factors. Then, by the fluctuation constant computation means, the voltage based on the resistance component, the voltage based on the reactance component and the resistance component and reactance component of the impedance of the external reference unit are substituted into the impedance computing equation (equation 1) stored in advance in the computing equation storing means and taking impedance fluctuations in consideration so as to compute fluctuation constants which are constants for fluctuation variables representing fluctuations based on impedance fluctuation factors. Thereby, numerically expressed fluctuations based on the impedance fluctuation factors can be determined. Further, by the bioelectrical impedance computation means, the fluctuation constants and the measured impedance of the living body are newly substituted into the impedance computing equation (equation 1) stored in advance in the computing equation storing means so as to compute the resistance component and reactance component of the true impedance of the living body. Thereby, accurate data with corrected fluctuations based on the impedance fluctuation factors can be obtained.

In the above embodiment, the external reference unit which is a known impedance (e.g., R=100 Ω, X=0 Ω) corresponding to the lower limit of the measurement range of bioelectrical impedance and the external reference unit which is a known impedance (e.g., R=800 Ω, X=0 Ω) corresponding to the upper limit of the measurement range of bioelectrical impedance are measured. However, the present invention can also be practiced by measuring the same external reference unit in place of the two different external reference units.

Further, although it has been described that the measurement means has an internal reference unit, the present invention can also be practiced with measurement means having no internal reference unit. When the measurement means has an internal reference unit as described with respect to the above embodiment, the effect of the impedance measurement method (refer to Japanese Patent No. 2,835,656) cited in Description of the Related Art, i.e., an effect that measurement of an impedance is not influenced by fluctuations by environmental changes of a constant current source, can be enjoyed.

In addition, in STEP S32 where the resistance component $R_B$ and reactance component $X_B$ of the true impedance of the living body are computed and output, the true impedance $Z_B$ of the living body may be output from the resistance component $R_B$ and the reactance component $X_B$.

Figure 7:
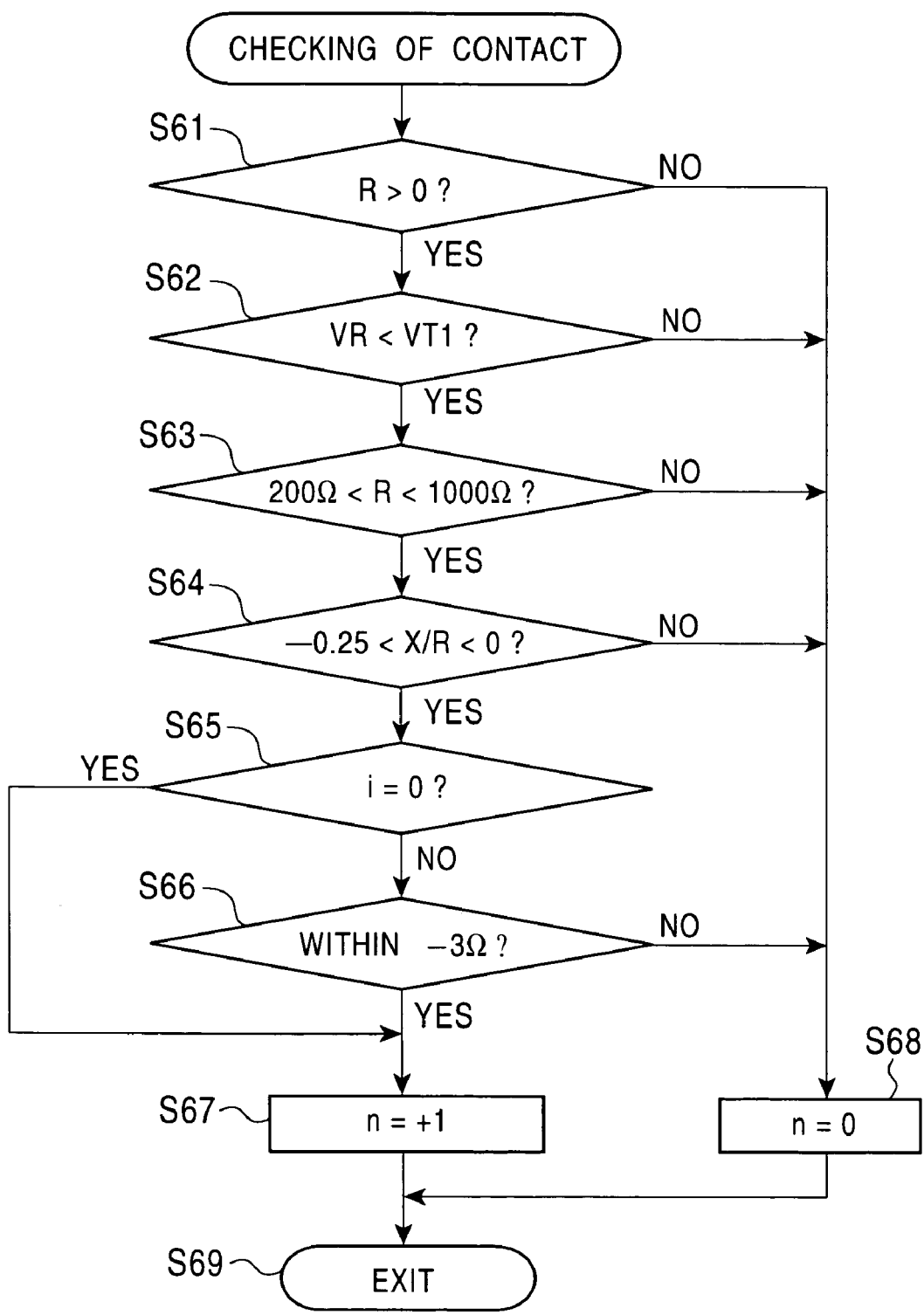
FIG. 7 is a flowchart illustrating a contact condition determination subroutine in the flowchart of FIG. 4.

Next, the contact condition determination routine in STEP S8 will be described by use of FIG. 7. Contact determination is made by using a number of checks.

Firstly, it is checked whether the complex voltage $V_B$ which has occurred in the living body 5 and has been measured in STEP S7 is a positive value (STEP S61). When $V_B$ is a negative value, it indicates that measurement results with the living body clearly not in contact with the electrodes have been obtained, thereby informing the subject of improper contact at this point.

Then, it is checked whether the voltage $V_{RR}$ measured based on the impedance component of the internal reference unit 7 which is obtained in STEP S22 is a larger value than a threshold voltage $VT_1$ which is stored in advance. The threshold voltage $VT_1$ is set at a half of a voltage obtained when the contact of the living body is normal. When $V_{RR}$ is smaller than $VT_1$, it is determined that the contact is not normal (STEP S62).

Then, it is checked whether the value of the resistance component $R_B$ of the true impedance of the living body 5 which has been computed in STEP S7 is within a normal range. The normal range is 200 Ω<$R_B$<1000 Ω. When the value of $R_B$ does not fall within this range, it is determined that the contact is not normal (STEP S63).

Figure 8:
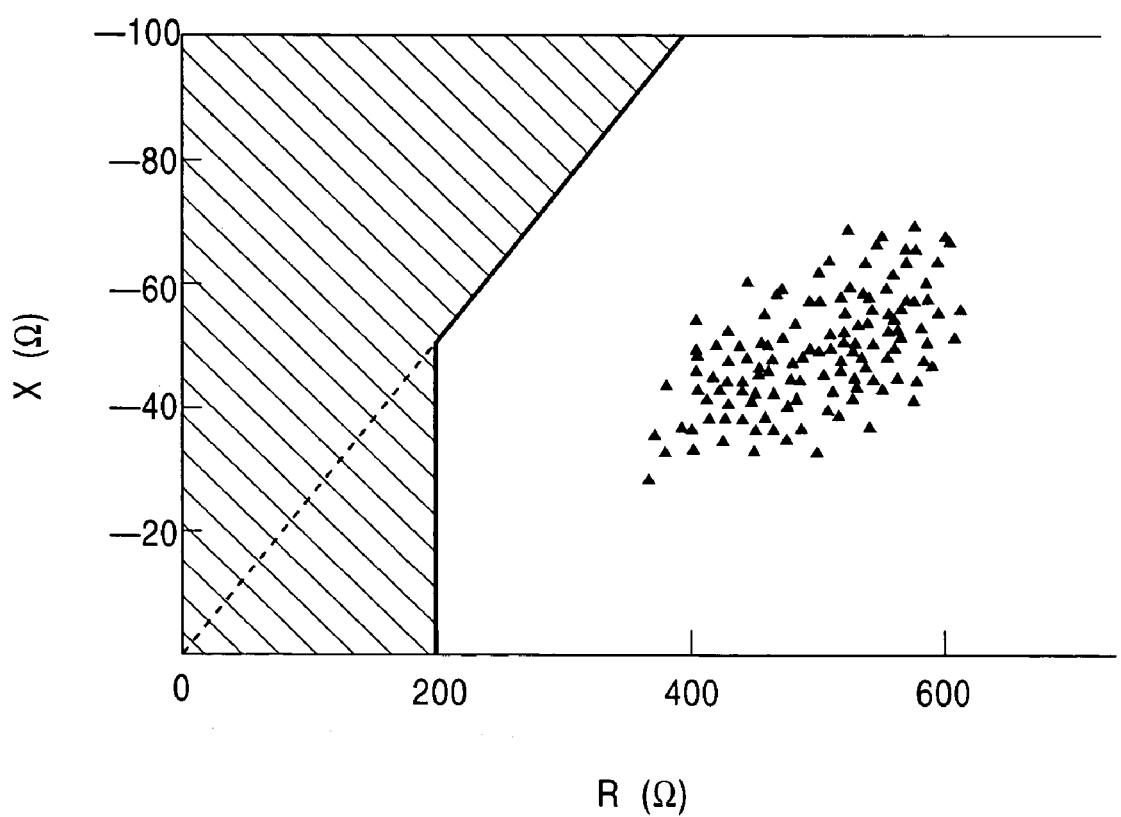
FIG. 8 is a graph prepared by plotting the results of computations of the resistance components R and reactance components X of several subjects.
Figure 9A:
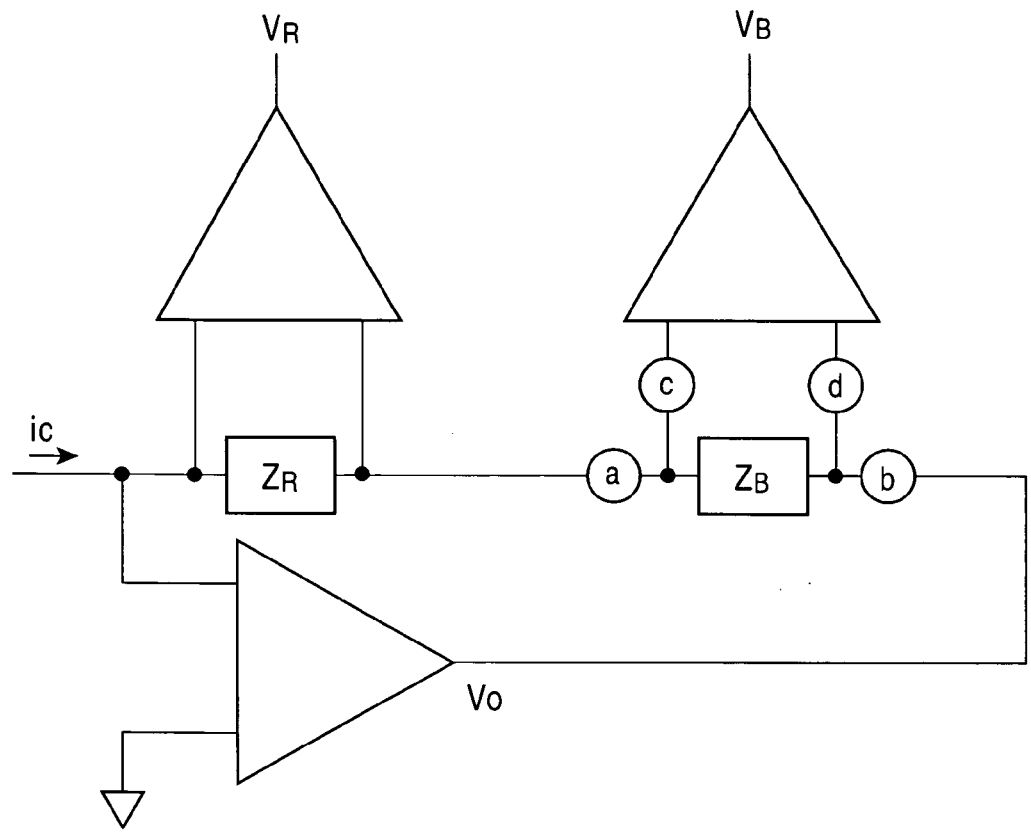
FIGS. 9A & 9B are block diagrams of a bioelectrical impedance measuring section for illustrating the background art.
Figure 9B:
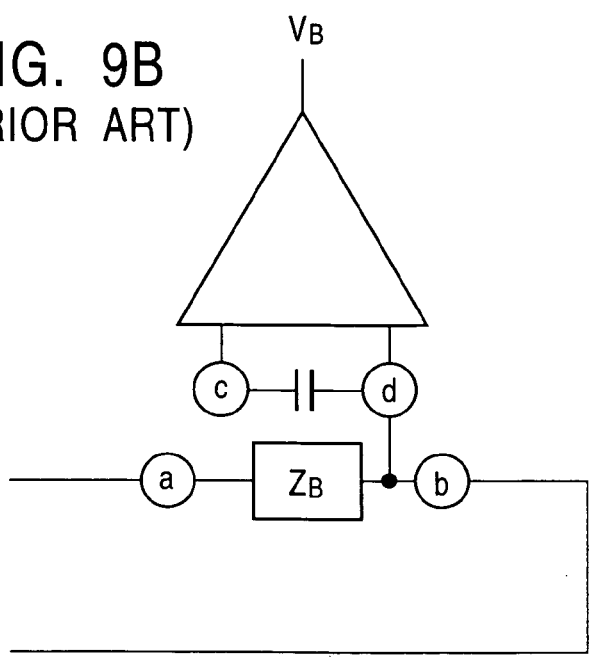

Then, it is checked whether a parameter for the phase difference of the living body 5 is within a normal range. As the parameter associated with the phase difference, the value of X/R (=tan θ) is used. To examine this value, the present inventor has actually measured an impedance between both feet and computed an R component and an X component for a number of subjects. A graph prepared by plotting the values thereof is shown in FIG. 8. As is clear from the graph, the R component between both feet of the living body is a value which falls within a range of about 300 to 700 Ω, and the X component between both feet of the living body is a value which falls within a range of −20 to −90 Ω. That is, the resistance component R and reactance component X of the impedance between both feet of the living body are within predetermined ranges, and when measurement values are out of the normal ranges, it can be determined that the contact is not normal.

Thus, in this case, a condition −0.25<X/R<0 is set, and the contact condition is determined by checking whether the value of X/R is within this range (STEP S64).

The shaded area in FIG. 8 is an area where the range 200 Ω<R within 200 Ω<R<1000 Ω in STEP S63 and the range −0.25<X/R within −0.25<X/R<0 in STEP S64 are combined. When the value is within such an area, it indicates that the living body is clearly not in contact with the electrodes, and it can be understood that determination of the contact condition in the present invention is valid accordingly.

Then, the resistance component R measured this time is compared with R measured by the bioelectrical impedance measuring routine the last time so as to determine whether a stable value is retained. However, if the number i of normal contacts is less than 0, this determination is not made since it is a first normal contact condition (STEP S65). When the number i of normal contacts is not 0, the value measured this time is compared with the measurement value of the last time. In this case, the resistance component R measured this time is compared with the resistance component R measured the last time so as to determine whether the difference between the two components R is within ±3 Ω (STEP S66). When the difference is ±3 Ω, it is determined that the contact is normal, and the number i of normal contacts is incremented by 1 (STEP S67).

Meanwhile, if at least one of the results of the determinations in STEPS S61, S62, S63, S64 and S66 is NO, it is determined that the contact condition is not normal, and the number i of normal contacts is set at 0 (STEP S68).

As described above, the number of normal contacts is determined according to the results of the determinations of the contact, whereby the contact condition determination routine is ended (STEP S69).

In the above-described example of the present invention, the method represented by STEPS S21 to S32 is used for calculations of the resistance component and the reactance component. Alternatively, a technique for determining the contact condition of the electrodes of the present invention by carrying out a bioelectrical impedance measurement by measurement currents of multiple frequencies and calculating resistance components and reactance components in accordance with the cole-cole circular arc law may be employed.

Further, in the above-described example, the contact condition is determined by the proper range of a value represented by X/R wherein R represents the resistance component of a bioelectrical impedance to be measured and X represents the reactance component of the bioelectrical impedance. Alternatively, it is also possible that a proper range is set for each of the values of the resistance component R and the reactance component X and the contact condition of the living body with the electrodes is determined by checking whether the components R and X are within the ranges.

Further, in the above-described example, the value represented by X/R is used as the parameter associated with a phase difference which is used for determination of the contact condition. However, the same effect as that of the present invention can still be obtained by use of a value represented by |X|/R or |X/R|.

Further, in this example, the resistance component and reactance component of true impedance are computed in the bioelectrical impedance measuring routine, and the contact condition is then determined in the contact condition determination routine. Since the determinations in STEPS S61 and S62 are possible if measurements of $V_B$ and $V_R$ are already done by the time STEP S32 for calculating the true impedance is carried out, the calculation of the true impedance in STEP S32 can be omitted if it is set to be performed during the contact condition determination routine (for example, between STEP S62 and STEP S63) and if the contact condition is determined to be not normal at that point.

Further, the present invention has been described as a determination method using a bioelectrical impedance value (Z=R+jX). If it is considered as admittance (Y=1/R+1/X=G+jB) and G/B wherein G represents conductance and B represents susceptance is used in place of R/X, a parameter associated with a phase difference is still used as in the present invention and determination of the contact condition can still be made.

In addition, in the present invention, the value represented by X/R is described as a parameter associated with a phase angle. However, it is generally known that there is a relationship $\tan^{-1} 2\pi ft = X/R$, and the same effect as that of the present invention can be obtained by using t as a parameter associated with a phase difference.

What is claimed is:

1. A bioelectrical impedance measuring apparatus comprising:
an impedance measurement unit for measuring a bioelectrical impedance which comprises electrodes to contact with a living body, and
a determination unit for determining the contact condition of the living body with the electrodes by use of a parameter associated with a phase difference of a true impedance of the living body, the true impedance being represented by fluctuation variables representing fluctuations based on impedance fluctuation factors occurring in the impedance measurement unit, and by voltage variables representing a voltage based on a resistance component of the bioelectrical impedance measured by the impedance measurement unit and a voltage based on a reactance component of the bioelectrical impedance measured by the impedance measurement unit.

2. The apparatus of claim 1, wherein when the resistance component in a bioelectrical impedance to be measured in the impedance measurement unit is represented by R and the reactance component in the bioelectrical impedance is represented by X, the parameter associated with the phase difference of the true impedance of the living body is a value represented by X/R.

3. The apparatus of claim 2, wherein the condition for determination of the contact in the determination unit is a<X/R<b (a and b are real numbers).

4. The apparatus of claim 3, wherein prior to determination of the contact condition of the living body with the electrodes by use of the parameter associated with the phase difference, the determination unit determines the contact condition by determining whether a parameter associated with the resistance component of the bioelectrical impedance to be measured in the impedance measurement unit is a positive value.

5. The apparatus of claim 4, wherein the parameter associated with the resistance component is a true impedance component variable representing the resistance component of the true impedance.

6. The apparatus of claim 4, wherein the parameter associated with the resistance component is a voltage variable based on the resistance component.

7. The apparatus of claim 3, wherein the real number a is set at "−0.25" and the real number b is set at "0".

8. A bioelectrical impedance measuring apparatus comprising:
an impedance measurement unit for measuring a bioelectrical impedance which comprises electrodes to contact with a living body, and
a determination unit for determining the contact condition of the living body with the electrodes by use of a parameter associated with a phase difference of a true impedance of the living body or an external reference unit,
wherein the true impedance is represented by a true impedance component variable $R_B$ indicating a resistance component of the true impedance of the living body or external reference unit, and a true impedance component variable $X_B$ indicating a reactance component of the true impedance of the living body or external reference unit,
wherein the true impedance is calculated by the following equation:

$$\begin{pmatrix} R_B \\ X_B \end{pmatrix} = \begin{pmatrix} C_R \\ C_X \end{pmatrix} \times \frac{\begin{pmatrix} V_{BR} \\ V_{BX} \end{pmatrix}}{\begin{pmatrix} V_{RR} \\ V_{RX} \end{pmatrix}} + \begin{pmatrix} V_{OSR} \\ V_{OSX} \end{pmatrix}$$

where the fluctuation variable $C_R$ indicates fluctuations based on a scale factor and phase of the resistance component of the living body or external reference unit; the fluctuation variable $C_X$ indicates fluctuations based on a scale factor and phase of the reactance component of the living body or external reference unit; the measured voltage variable $V_{BR}$ indicates a voltage based on the resistance component of the living body or external reference unit; the measured voltage variable $V_{BX}$ indicates a voltage based on the reactance component of the living body or external reference unit; the measured voltage variable $V_{RR}$ indicates a voltage based on a resistance component of an internal reference unit; the measured voltage variable $V_{RX}$ indicates a voltage based on a reactance component of the internal reference unit; the fluctuation variable $V_{OSR}$ indicates fluctuations based on an offset voltage in a resistance component axis direction; and the fluctuation variable $V_{OSX}$ indicates fluctuations based on an offset voltage in a reactance component axis direction.

9. The apparatus of claim 8, wherein the parameter associated with the phase difference is a value represented by $X_B/R_B$.

* * * * *